United States Patent
Kreft et al.

(10) Patent No.: US 6,800,764 B2
(45) Date of Patent: Oct. 5, 2004

(54) PROCESS FOR THE SYNTHESIS OF CHIRALLY PURE BETA-AMINO-ALCOHOLS

(75) Inventors: Anthony Frank Kreft, Langhorne, PA (US); Madelene Miyoko Antane, West Windsor, NJ (US); Derek Cecil Cole, New City, NY (US); Dennis Martin Kubrak, Philadelphia, PA (US); Lynn Resnick, Edison, NJ (US); Joseph Raymond Stock, Monroe, NY (US); Zheng Wang, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/304,322

(22) Filed: Nov. 26, 2002

(65) Prior Publication Data

US 2003/0144531 A1 Jul. 31, 2003

Related U.S. Application Data

(60) Provisional application No. 60/339,264, filed on Dec. 11, 2001.

(51) Int. Cl.$^7$ ...................... C07D 333/32; C07C 209/00
(52) U.S. Cl. .......................... 549/65; 564/302; 564/487; 564/489
(58) Field of Search ........................... 549/65; 564/302, 564/487, 489

(56) References Cited

U.S. PATENT DOCUMENTS

| | | | | |
|---|---|---|---|---|
| 2,440,356 A | | 4/1948 | Behrens et al. | |
| 4,105,696 A | * | 8/1978 | Hajos et al. | 568/312 |
| 4,990,669 A | * | 2/1991 | Reetz et al. | 564/391 |
| 5,367,073 A | * | 11/1994 | Singaram et al. | 544/170 |
| 5,449,778 A | | 9/1995 | Beylin et al. | |
| 5,512,682 A | * | 4/1996 | Hilpert | 548/477 |
| 5,767,254 A | * | 6/1998 | Polt | 536/17.2 |
| 5,783,701 A | * | 7/1998 | Tung et al. | 546/169 |
| 5,919,949 A | * | 7/1999 | Hilpert | 548/479 |
| 6,147,253 A | * | 11/2000 | Wieczorek | 562/43 |
| 6,156,940 A | * | 12/2000 | Saito et al. | 568/814 |
| 6,399,787 B1 | * | 6/2002 | Zhang | 548/469 |
| 6,410,749 B1 | * | 6/2002 | Katayama et al. | 548/478 |
| 6,541,645 B1 | * | 4/2003 | Canary et al. | 549/5 |
| 2002/0183361 A1 | | 12/2002 | Kreft et al. | |
| 2003/0013892 A1 | | 1/2003 | Kreft et al. | |

OTHER PUBLICATIONS

Solomons et al., "Fifth Edition—Organic Chemistry", John Wiley & Sons, New York, NY: 771 (1992).
P.D. Bailey, "Appendix A—Synthesis of Amino Acids", in *An Introduction to Peptide Chemistry*, John Wiley & Sons: New York, pp. 167–172 (1990).
Hassan et al., "Synthesis of Optically Active α–Amino Nitriles by Asymmetric Transformation of the Second Kind Using a Principle of O. Dimroth", *J. Chem. Soc., Perkin. Trans.*, 1:3747–3757 (1998).
Harris et al., "The Synthesis of Tenuazonic and Congeneric Tetramic Acids", *J. Med. Chem.*, 8:478–482 (Jul. 1965).
Zilg et al., "Stereochemical Aspects of Lotaustralin Biosynthesis", *J. Biol. Chem.*, 249(10):3112–3115 (May 25, 1974).
Eisler et al., "Amino Acids and Peptides. LXV. Analogues of Oxytocin with Isoleucine Replaced by L–Diethylalanine, L–Cyclopentylglycine, and L–and D–Cyclohexylglycine", *Coll. Czech. Chem. Commun.*, 31:4563–4580 (1966).
Prätorius et al., "Die Darstellund isoleucinverwandter L–α–Aminocarbonsäuren", *Chem. Ber.*, 108:3079–3090 (1975).
Vigneaud et al., "The Synthesis of DL–β,β–Diethylcysteine and DL–β–Ethyl–β–Methylcysteine", *J. Biol. Chem.*, 176:907–914 (1948).
Bailey et al., "Resolution of Racemic Mixtures", in *An Introduction to Peptide Chemistry*, John Wiley & Sons: New York, pp. 173–175 (1990).
Bailey et al., "Asymmetric Synthesis", in *An Introduction to Peptide Chemistry*, John Wiley & Sons: New York, pp. 175–181 (1990).
Han et al., "Total Asymmetric Synthesis of Highly Constrained Amino Acids β–Isopropyl–2',6'–Dimethyl–Tyrosines", *Tet. Lett.*, 38(29):5135–5138 (1997).
Burk et al., "Asymmetric Catalytic Synthesis of β–Branched Amino Acids via Highly Enantioselective Hydrogenation Reactions", *J. Am. Chem. Soc.*, 117:9375–9376 (1995).

* cited by examiner

*Primary Examiner*—Deborah C. Lambkin
(74) *Attorney, Agent, or Firm*—Howson and Howson

(57) ABSTRACT

A process is provided for preparing chirally pure S-enantiomers of α-amino acids comprising the steps of: a) preparing an organometallic reagent from an alkyl halide of the formula $(R)_2CH(CH_2)_nCH_2X$; b) adding the organometallic reagent to carbon dioxide to afford a carboxylic acid; c) activating the carboxylic acid with an acid chloride, phosphorus trichloride, acid anhydride, or thionyl chloride in the presence of a tertiary amine base; d) reacting the product of step c) with an alkali metal salt of S-4-benzyl-2-oxazolidinone; e) treating the product of step d) with a strong non-nucleophilic base to form an enolate anion; f) trapping the enolate anion with 2,4,6-triisopropylbenzenesulfonyl azide to afford an oxazolidinone azide; g) hydrolyzing the oxazolidinone azide with an aqueous base to afford an α-azido acid; h) reducing the α-azido acid to the α-amino acid; and i) recrystallizing the α-amino acid to the chirally pure α-amino acid. A process is also provided for preparing chirally pure S-enantiomers of β-amino alcohols further comprising the steps of reducing the crude α-amino acid to the β-amino alcohol and recrystallizing the β-amino alcohol to the chirally pure β-amino alcohol. A process is further provided for preparing chirally pure S enantiomers of N-sulfonyl β-amino alcohols further comprising the steps of sulfonylating the β-amino alcohol with 5-chloro-thiophene-2-sulfonyl halide; and recrystallizing to afford the chirally pure N-sulfonyl β-amino alcohols.

47 Claims, No Drawings

PROCESS FOR THE SYNTHESIS OF CHIRALLY PURE BETA-AMINO-ALCOHOLS

CROSS-REFERENCE TO RELATED APPLICATIONS

This application claims the benefit of the priority of U.S. Provisional Patent Application No. 60/339,264, filed Dec. 11, 2001.

BACKGROUND OF THE INVENTION

This invention relates to a novel process of producing chirally pure β-amino-alcohols, as well as intermediates thereof including α-amino acids. Compounds of the present invention are useful for a variety of purposes, including for use in pharmaceutical compositions.

A variety of techniques have been described for production of a preferred enantiomer from α-amino acids. These techniques require the use of either resolution procedures or asymmetric syntheses at some point in the synthesis to prepare the target compounds. More efficient means for producing chirally pure target compounds are needed.

SUMMARY OF THE INVENTION

In one aspect, the present invention comprises a process for preparing chirally pure S-enantiomers of α-amino acids.

In a further aspect, a process is provided for preparing chirally pure S-enantiomers of β-amino alcohols.

In yet another aspect, a process is provided for preparing chirally pure S-enantiomers of N-sulfonyl β-amino alcohols.

These and other aspects of the invention will be apparent to one of skill in the art upon reading of the following detailed description of the invention.

DETAILED DESCRIPTION OF THE INVENTION

The present invention is directed to a process for the preparation of chiral α-amino acids of the formula $(R)_2CH(CH_2)_nCH(NH_2)C(=O)OH$, where n is 0 to about 10; chiral β-amino alcohols of the formula $(R)_2CH(CH_2)_nCH(NH_2)CH_2OH$; and chiral S enantiomers of N-sulfonyl β-amino alcohols of the formula $(R)_2CH(CH_2)_nCH(CH_2OH)NH-S(O)_2-2-C_4H_2S-5-Cl$, wherein R is lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, or CH(OH)-4-SCH$_3$-phenyl.

Both natural and unnatural α-amino acids, natural and unnatural β-amino alcohols, and intermediates thereof, may be prepared according to the present invention. Such α-amino acids and β-amino alcohols may also be referred to as 2-amino acids or 2-amino alcohols.

As used herein, the term "chirally pure" refers to compounds which are in 100% S-enantiomeric form as measured by chiral high performance liquid chromatography (HPLC). Other methods of measuring chiral purity include conventional analytical methods, including specific rotation, and conventional chemical methods. However, the technique used to measure chiral purity is not a limitation on the present invention.

As described herein, the method of the invention affords chirally pure α-amino acids or β-amino alcohols following the recrystallization step in the method. Where chiral purity is not a requirement, the method of the invention may also be used to provide chiral α-amino acids or β-amino alcohols which contain some percentage of a mixture of enantiomeric forms, e.g., which may be composed of about 90 to about 99% S-enantiomers, by following the method of the invention in the absence of recrystallization.

In one embodiment, the present invention is directed toward a process for preparing chiral S-enantiomers of α-amino acids, which involves preparing an organometallic reagent from an alkyl halide of the formula $(R)_2CH(CH_2)_nCH_2X$, wherein X is Cl, Br or I and n is 0 to about 10; adding the organometallic reagent to carbon dioxide to afford a carboxylic acid; activating the carboxylic acid with an acid halide, phosphorus trichloride, acid anhydride, or thionyl chloride in the presence of a tertiary amine base; reacting the product of the activating step with an alkali metal salt of S-4-benzyl-2-oxazolidinone; treating the product of the alkali metal step with a strong non-nucleophilic base to form an enolate anion; trapping the enolate anion with 2,4,6-triisopropylbenzenesulfonyl azide to afford an oxazolidinone azide; hydrolyzing the oxazolidinone azide with an aqueous base to afford an α-azido acid; reducing the α-azido acid to the α-amino acid; and recrystallizing the α-amino acid to afford the chirally pure α-amino acid.

In another embodiment, the present invention is directed toward a process for preparing chiral S enantiomers of β-amino alcohols, which involves preparing an α-amino acid as described above, reducing the α-amino acid to the β-amino alcohol, and recrystallizing the β-amino alcohol to afford the chirally pure β-amino alcohol.

In a further preferred embodiment, the present invention is directed toward a process for preparing chiral S enantiomers of N-sulfonyl β-amino alcohols of the general formula:

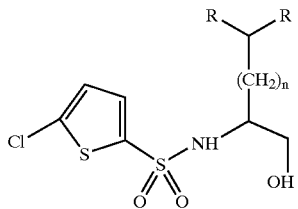

wherein R is lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, or CH(OH)-4-SCH$_3$-phenyl and n is 0 to about 10. This process involves reducing an α-amino acid to an β-amino alcohol of the formula $(R)_2CH(CH_2)_nCH(NH_2)CH_2OH$; sulfonylating the β-amino alcohol with 5-chloro-thiophene-2-sulfonyl halide; and recrystallizing the product of the sulfonylation step to afford the chirally pure N-sulfonyl β-amino alcohols.

In one embodiment, the compounds of the invention contain one chiral carbon center, where R in the above-noted structures is the same. In certain desired embodiments, the R groups are methyl, ethyl, and n-propyl, and most preferably the R groups are ethyl. However, the invention further encompasses producing α-amino acids and β-amino alcohols of the general formulae provided herein where the R groups are different. In these compounds one or more additional chiral centers may be present; however, the additional chiral centers must be optically pure and must not interfere with the production of the chirally pure α-amino acids, β-amino alcohols, and pure S enantiomers of N-sulfonyl β-amino alcohols of the present invention.

In another preferred embodiment, the chiral carbon center is of S-stereochemistry which gives rise to enantiomerically pure products.

Thus, the process of the invention provides an efficient route to the synthesis of chirally pure S enantiomers of β-amino alcohols, and intermediates thereof, which are useful for a variety of purposes. For example, the exemplary compounds provided herein, the N-sulfonyl β-amino alcohols are useful for inhibition of β-amyloid production, which is implicated in amyloid angiopathy, cerebral amyloid angiopathy, systemic amyloidosis, Alzheimer's Disease (AD), hereditary cerebral hemorrhage with amyloidosis of the Dutch type, inclusion body myositis, Down's syndrome, among others.

As used herein, the term "pharmaceutically useful" refers to compounds having a desired biological effect, whether as a therapeutic, immune stimulant or suppressant, adjuvant, or vaccinal agent. Similarly, a variety of compounds which are suitable for use in non-pharmaceutical applications, e.g., a diagnostic, a marker, among others may be produced by the method of the invention. However, other pharmaceutically useful compounds may be produced by this method.

The term "alkyl" is used herein to refer to both straight- and branched-chain saturated aliphatic hydrocarbon groups having one to ten carbon atoms, preferably one to eight carbon atoms and, most preferably, one to six carbon atoms; "alkenyl" is intended to include both straight- and branched-chain alkyl groups with at least one carbon—carbon double bond and two to eight carbon atoms, preferably two to six carbon atoms; and "alkynyl" group is intended to cover both straight- and branched-chain alkyl groups with at least one carbon—carbon triple bond and two to eight carbon atoms, preferably two to six carbon atoms. As used herein, the term "lower" refers to any of the above-defined groups having one to six carbon atoms.

The terms "substituted alkyl", "substituted alkenyl", "substituted alkynyl", "substituted lower alkyl", "substituted lower alkenyl", and "substituted lower alkynyl" refer to alkyl, alkenyl, alkynyl, lower alkyl, lower alkenyl, and lower alkynyl as just described having from one to three substituents which are independently selected from among halogen, CN, OH, $NO_2$, amino, aryl, heterocyclic, substituted aryl, substituted heterocyclic, alkoxy, substituted alkoxy, aryloxy, substituted aryloxy, alkylcarbonyl, alkylcarboxy, alkylamino, and arylthio. These substituents may be attached to any carbon of an alkyl, alkenyl, or alkynyl group provided that the attachment constitutes a stable chemical moiety.

The term "substituted phenyl" refers to a phenyl group having one to four substituents which are independently selected from among halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "cycloalkyl" refers to a carbon-based ring having more than 3 carbon atoms contained in the backbone of the ring.

The term "substituted benzyl" refers to a benzyl group having one to four substituents which are independently selected from among halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "halogen" refers to chlorine, bromine, fluorine, or iodine.

The term "strong non-nucleophilic base" refers to a non-nucleophilic basic reagent, which does not act as a nucleophile or bind to the reagents utilized according to the reaction. A number of non-nucleophilic bases are known in the art and include sodium hydride, potassium hydride, lithium diisopropylamide and potassium hexamethyldisilazide.

The term "aqueous base" refers to a solution composed of at a minimum a base and water. A number of bases which readily dissolve in water are known in the art and include alkali metal hydroxides such as lithium hydroxide, sodium hydroxide or potassium hydroxide, among others. The aqueous base solution may further contain other reagents which do not interfere with the reactions of the present invention, and include organic solvents such as tetrahydrofuran, methanol, or hydrocarbon solvents, salts such as sodium chloride, and buffers, among others.

The term "organic solvent" may include any solvent known in the art, which does not react with the reagents utilized in the reaction and includes saturated hydrocarbon solvents, unsaturated hydrocarbon solvents, including aromatic hydrocarbon solvents, alcohols, halocarbons, ethers, and acetates, among others.

The compounds of the present invention can be used in the form of salts, e.g., derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include salts with alkali metals or alkaline earth metals, such as sodium (e.g., sodium hydroxide), potassium (e.g., potassium hydroxide), lithium, calcium or magnesium.

These salts, as well as other compounds of the invention may be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233–241, ed., John Wiley & Sons (1996).

In one embodiment, the α-amino acids and β-amino alcohols of the invention are reacted with a variety of reagents to form complexes having at least one chiral carbon center. In one embodiment, the α-amino acids and alcohols are reacted with thiophene sulfonyl halides, more desirably, 5-halo thiophene sulfonyl halides, and most desirably, 5-chloro-thiophene sulfonyl halides to form the chirally pure heterocyclic N-sulfonyl β-amino-alcohols of formula (8).

In another embodiment, the α-amino acids or β-amino alcohols of the invention are reacted with furansulfonyl halides to form chirally pure heterocyclic N-sulfonyl β-amino-alcohols.

The following scheme (Scheme 1) will facilitate further a general understanding of the invention by those skilled in the art, while Scheme 2 describes a preferred embodiment of the instant invention. Those skilled in the art will readily understand how to apply the process of this invention to the various embodiments encompassed by this invention.

Scheme 1

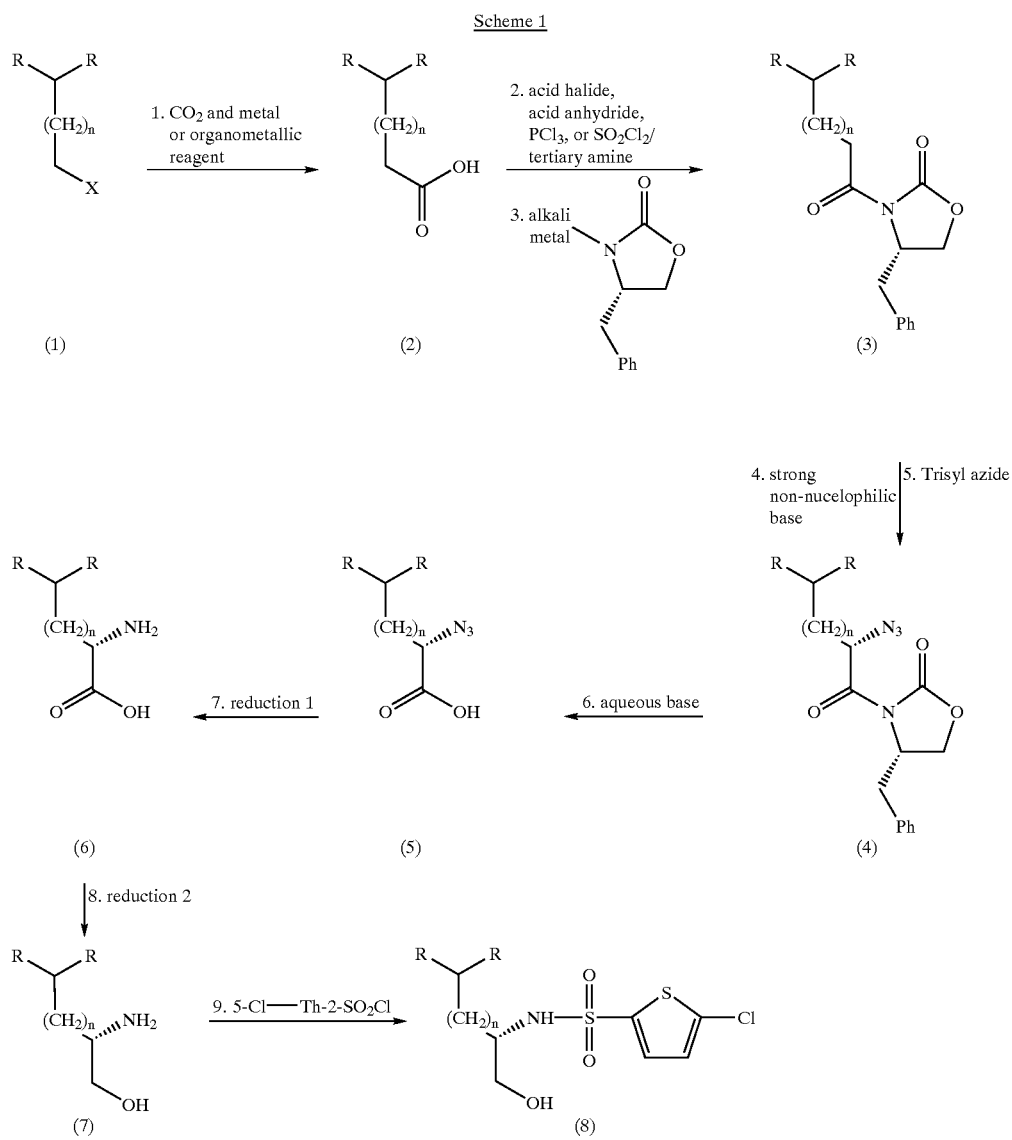

Referring to Scheme 1, conversion of the alkyl halide (1) to the carboxylic acid (2) may be achieved by initial conversion of the alkyl halide (1) to an organometallic reagent. Various techniques are known in the art to convert alkyl halides to organometallic reagents. See, e.g., *Organometallic Syntheses*, Volume 2, John J. Eisch, ed., Academic Press, New York, 1981. Preferably, the alkyl halide is an alkyl bromide, chloride, or iodide. More preferably, the alkyl halide is an alkyl bromide. A variety of metals and organometallic reagents are known to facilitate conversion of alkyl halides to carboxylic acids and include Grignard reagents, organolithium reagents, magnesium and lithium metals, among others. Once prepared, the organometallic reagent is converted to a carboxylic acid, preferably by quenching with carbon dioxide. Alternatively, conversion to the carboxylic acid may be by any other suitable method known in the art. Such methods include reacting the organometallic reagent with diethyl carbonate or ethyl chloroformate to afford the ethyl ester, which is hydrolyzed to the carboxylic acid using an aqueous base. A variety of aqueous bases may be selected by one of skill in the art, and include alkali metal hydroxides such as lithium hydroxide, sodium hydroxide or potassium hydroxide, among others.

The carboxylic acid (2) is then converted to the oxazolidinone derivative (3). The carboxylic acid (2) is first converted to an activated carbonyl species by reaction of the carboxylic acid with a reagent, including, but not limited to, acid halides, phosphorus trichloride, acid anhydrides, or thionyl chloride, followed by reaction with a tertiary amine. A variety of acid halides may be utilized and include acid chlorides, bromides, and iodides. Preferably, the acid halide is an acid chloride. A variety of acid chlorides are known in the art and include pivaloyl chloride, isovaleryl chloride, ethyl chlorocarbonate, and isobutyl chlorocarbonate, among others. Most preferably, the acid chloride is pivaloyl chloride. A variety of acid anhydrides are known in the art and include trifluoroacetic anhydride and trichloroacetic anhydride. Preferably, the acid anhydride is trifluoroacetic anhydride. A number of tertiary amines are known in the art and include triethylamine, trimethyl amine, N,N-diisopropylethyl amine, and pyridine, among others. Preferably, the tertiary amine is triethylamine.

The activated carbonyl species is subsequently reacted with an alkali metal salt of a chiral auxiliary reagent in a suitable organic solvent. Preferably, the chiral auxiliary agent is S-4-benzyl-2-oxazolidinone. However, other chiral auxiliaries may be utilized and readily selected by one of skill in the art. See, e.g., *Principles and Applications of Asymmetric Synthesis*, G. Lin, Y. Li, and A. Chan, Wiley-Interscience, New York, 2001 (for example, page 104, Tables 2–13). Alkali metal salts of S-4-benzyl-2-oxazolidinone which are useful in this reaction include lithium, sodium, and potassium salts. Preferably, the chiral auxiliary is the lithium salt of S-4-benzyl-2-oxazolidinone.

In an effort to maximize product yield, conversion of the acid to the oxazolidinone derivative is preferably performed in about 30 minutes. However, the reaction time may be dependent upon a variety of factors including reaction temperature, purity of the reagents, scale of the reaction, environmental conditions, exact structure of the substrate, and concentration, among others. Longer or shorter reaction times (e.g., 10 to about 60 minutes) may be utilized as determined by one of skill in the art.

(generated by the action of n-butyllithium on S-4-benzyl-2-oxazolidinone) in tetrahydrofuran (THF) to form the oxazolidinone derivative (3). See, Scheme 2.

The oxazolidinone derivative (3) is then converted to its enolate anion by the action of a strong non-nucleophilic base, as defined herein. Preferably, the strong non-nucleophilic base is potassium hexamethyldisilazide. The enolate anion is then reacted with trisyl azide to form the azido-oxazolidinone intermediate (4).

The azido-oxazolidinone intermediate (4) can be converted to the α-azido-acid (5) by any suitable method known in the art. In a preferred embodiment, the azido-oxazolidinone intermediate is converted to the α-azido acid by hydrolysis with an aqueous base, as defined herein. Preferably, the azido-oxazolidinone intermediate is converted to the α-azido acid by hydrolysis using an aqueous solution of lithium hydroxide.

The α-azido-acid (5) can be reduced to the α-amino-acid (6) by any suitable method known in the art. Preferably, the

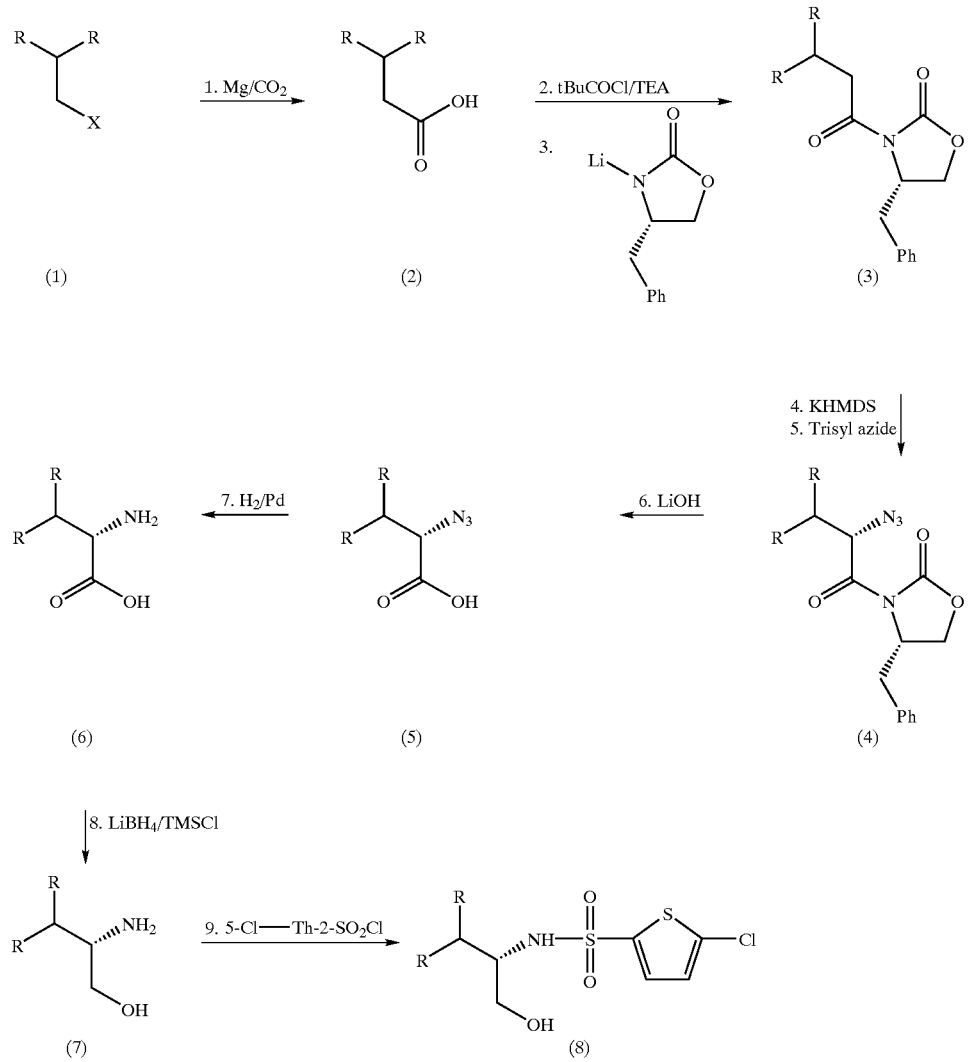

In a preferred embodiment, the carboxylic acid (2) is converted to the mixed anhydride by reaction with pivaloyl chloride in the presence of triethylamine and subsequently reacted with the lithium salt of S-4-benzyl-2-oxazolidinone reduction is performed using catalytic reduction with hydrogen gas in the presence of 10% palladium on carbon catalyst. Alternatively, the reduction may be performed with zinc/HCl, sodium borohydride, or aqueous triphenyl phosphine.

In an effort to maximize product yield, the reduction is desirably performed in about 24 hours. However, the reaction time may be dependent upon a variety of factors including reaction temperature, purity of the reagents, scale of the reaction, environmental conditions, exact structure of the substrate, and concentration, among others. Longer or shorter reaction times (e.g., about 12 hours to about 96 hours) may be utilized as determined by one of skill in the art.

The chiral α-amino acid may then be isolated using techniques known by those of skill in the art including, but not limited to, chromatography and recrystallization. Recrystallization may be performed using a variety of organic and inorganic solvents known in the art and provides chirally pure α-amino acids.

Alternatively, the α-amino acid (6) can be reduced to the β-amino alcohol (7) by a variety of methods known in the art. In a preferred embodiment, reduction of the α-amino acid is accomplished with catalytic hydrogenation, diborane, related boranes such as catecholborane, lithium borohydride/trimethyl silyl chloride (TMSCl), lithium aluminum hydride, diisobutyl aluminum hydride (DiBAL-H), bis(2-methoxyethoxy) aluminum hydride (Red-Al), and alane. More preferably, the reduction is accomplished using lithium borohydride/TMSCl over 48 hours.

The chiral β-amino alcohol may then be isolated using techniques known by those of skill in the art including, but not limited to, chromatography and recrystallization. Recrystallization may be performed using a variety of organic and inorganic solvents known in the art.

Alternatively, the β-amino-alcohol (7) is converted to the target chiral compound (8) by reaction with 5-chloro-thiophene-2-sulfonyl chloride in the presence of a strong non-nucleophilic base such as a tertiary amine or alkali metal hydroxide. Recrystallization using an appropriate solvent system using techniques known in the art affords the chirally pure target compound.

The concise nature of the reaction sequence, ease of synthesis, scalability and abundance of potential starting materials makes this process a practical method for the preparation of chirally pure S enantiomers of N-sulfonyl β-amino alcohols.

Where catalysts or solvents are included in a reaction step of this invention, it is expected that other catalysts or solvents known in the art, but not mentioned herein, may be used; those skilled in the art will readily be able to determine suitable catalysts, solvents and reaction conditions for each reaction step included in the invention.

The invention includes certain types of reactions, such as enolate trapping, hydrolysis and reduction reactions, that are generally known in the art, but previously had not been applied in the novel manner of the present invention. Variations in the specific methods of accomplishing individual steps of the invention may be apparent to those in the art. Although all these possible variations cannot be set forth herein, such variations are contemplated to be within the scope of the present invention.

The following examples are provided to illustrate the production and activity of representative compounds of the invention and to illustrate their performance in a screening assay. One skilled in the art will appreciate that although specific reagents and conditions are outlined in the following examples, these reagents and conditions are not a limitation on the present invention.

EXAMPLES

Example 1

3-Ethylpentanoic Acid

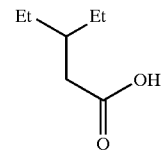

Into a 2 L 3-necked flask equipped with a condenser attached to a nitrogen inlet tube, a mechanical stirrer, and a 500 mL addition funnel, was added magnesium turnings (18.7 g, 0.769 mol), which were crushed in a mortar and pestle. The reaction was placed under argon. Enough THF was added to just cover the magnesium turnings. With the mechanical stirrer turned off, 2-ethyl-1-bromobutane (155.5 g 0.70 mol) was placed in the addition funnel and about 2–3 mL was added to the magnesium turnings. This area of the THF solution was then heated with a heat gun until vigorous boiling occurred. The remaining 2-ethyl-1-bromobutane was diluted with THF (200 mL) and added dropwise to the stirred reaction mixture at a rate that maintained a gentle reflux. The addition was completed in approximately 3–4 h. After 24 h, the gray slurry was diluted with THF (500 mL), and gently heated with a hot water bath until a homogeneous solution was formed. The warm solution was then poured into two 4 L Nalgene beakers each containing crushed solid carbon dioxide (1 L). The slush was stirred well with a Teflon rod and allowed to stand at room temperature. After 18 h, the solutions were diluted with ethyl acetate (500 mL), and washed with 2N hydrochloric acid (500 mL). The aqueous layer was saturated with sodium chloride and extracted once more with ethyl acetate (500 mL). The combined ethyl acetate layers were dried ($Na_2SO_4$). Concentration under reduced pressure gave a wet residue, which was taken up in methylene chloride (600 mL), dried ($Na_2SO_4$), and concentrated at 56° C. under reduced pressure to give the title compound as an oil (91 g, 99.8%): $^1$H NMR (DMSO-d$^6$, 500 MHz): δ11.95 (broad s, 1H), 2.11 (d, J=6.9 Hz, 2H), 1.60 (septet, J=6.5 Hz, 1H), 1.28 (m, 4H), 0.81 (t, J=7.5 Hz, 6H); MS(−ESI): [M—H]$^-$, 129 (100%); Anal. Calc. for $C_7H_{14}O_2$: C, 64.58; H, 10.84. Found: C, 64.61; H, 11.11.

Example 2

(3(2S), 4S)-3-(3-Ethyl-1-oxopentyl)-4-(phenylmethyl)-2-oxazolidinone

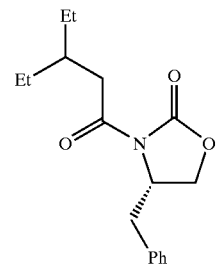

Into a 3 L 3-necked flask equipped with a nitrogen inlet tube, mechanical stirrer, and addition funnel with a stopper, was added the product from Example 1 (91 g, 0.699 mol) and THF (1 L). The solution was placed under nitrogen and cooled to −78° C. Triethylamine (102.3 mL, 0.734 mol) was added, followed by pivaloyl chloride (90.4 mL, 0.734 mol). The −78° C. bath was replaced with an ice bath. The thick slurry was stirred at 0° C. for 1 h.

Concurrently, into a 5 L 3-necked flask equipped with a stopper, mechanical stirrer, and nitrogen inlet, was added (S)-(−)-4-benzyl-2-oxazolidinone (136 g, 0.767 mol) and THF (1 L). The reaction mixture was placed under nitrogen and cooled to −78° C. A solution of n-butyllithium (480 mL of a 1.6 M solution in hexanes, 0.768 mol) was added. The resulting solution was stirred at −78° C. for 40 min. The thick slurry of the mixed anhydride was re-cooled to −78° C. for 10 min, then poured through a powder funnel into the lithium enolate solution of (S)-(−)-4-benzyl-2-oxazolidinone. The reaction mixture was allowed to warm slowly to room temperature overnight. The reaction mixture was divided into three 1 L-portions. Each portion was diluted with ethyl acetate (800 mL), washed once with saturated potassium phosphate monobasic (300 mL), twice with ice:1N NaOH (1:1, 300 mL), once with saturated potassium phosphate monobasic (300 mL), once with brine (300 mL), and dried (Na$_2$SO$_4$). After concentration under reduced pressure the crude residue was passed through a plug of Silica Gel (1 kg) with hexane and ethyl acetate to yield an amber oil (123.7 g, 61%): Opt. Rot. [α]$_D^{25}$=+94.75° (1% solution, DMSO); $^1$H NMR (DMSO-d$^6$, 500 MHz): δ7.35-7.15 (m, 5H), 4.65 (m, 1H), 4.31 (t, J=8.6 Hz, 1H), 4.17 (dd, J=2.8, 8.9 Hz, 1H), 3.00 (dd, J=3.2, 13.4 Hz, 1H), 2.91 (dd, J=7.7, 13.5 Hz, 1H), 2.81 (dd, J=6.7, 16.2 Hz, 1H), 2.69 (dd, J=6.9, 16.2 Hz, 1H), 1.80 (septet, J=6.4 Hz, 1H), 1.32 (m, 4H), 0.84 and 0.83 (two overlapping triplets, J=7.3 Hz, 6H); $^{13}$C NMR (DMSO-d$^6$, 100 MHz): δ172.15, 153.27, 135.65, 129.39, 128.47, 126.81, 65.96, 54.26, 38.41, 36.70, 36.19, 25.07, 24.98, 10.62, 10.52; MS(+ESI): [M+H]$^+$ 290 (100%); Anal. Calc. for C$_{17}$H$_{23}$NO$_3$: C, 70.56; H, 8.01; N, 4.84. Found: C, 70.69; H, 8.31; N, 4.83. Analytical HPLC (4.6 mm×100 mm Chromolith Monolith column, eluant 70:30 AcCN/water each containing 0.1% TFA, isocratic, flow rate=4 mL/min, UV detection at 254 nm) indicates a major component (97.7%).

Example 3

(3(2S), 4S)-3-(2-Azido-3-ethyl-1-oxopentyl)-4-(phenylmethyl)-2-oxazolidinone

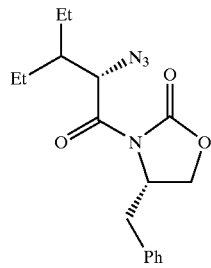

Into a 12 L 3-necked flask, equipped with a nitrogen inlet tube, a mechanical stirrer, and a 500 mL addition funnel with a stopper, was added the product from Example 2 (122.8 g, 0.424 mol) and THF (943 mL). The solution was placed under nitrogen and cooled to −78° C. A solution of potassium bis(trimethylsilyl) amide (1.018 L of a 0.5 M solution in toluene, 0.509 mol) in THF (943 mL) was added dropwise over a period of 2.5 h. After stirring at −78° C. for 1 h, a pre-cooled (−78° C., 50 min) solution of 2,4,6-triisopropylbenzenesulfonyl azide (170.6 g, 0.55 mol) in THF (573 mL) was added via cannula (two 18 gauge double tipped needles) over a period of 14 min. After an additional 9 min at −78° C., glacial acetic acid (111.7 mL, 1.95 mol) was added all at once through a funnel. After 2 min at −78° C., anhydrous potassium acetate (166.5 g, 1.70 mol) was added. The −78° C. bath was lowered, and the reaction mixture was allowed to stir at room temperature overnight. The reaction mixture was divided into four-1 L portions, and each portion was diluted with ethyl acetate (400 mL), washed twice with saturated potassium phosphate monobasic (400 mL), once with brine (400 mL), and dried (Na$_2$SO$_4$). After concentration under reduced pressure the crude residue was passed through a plug of Silica Gel (1 kg) with hexane and ethyl acetate to give an oil (79 g, 56%): Opt. Rot. [α]$_D^{25}$=+112.16° (1% solution, DMSO); $^1$H NMR (DMSO-d$^6$, 500 MHz): δ7.35-7.15 (m, 5H), 5.11 (d, J=6.1 Hz, 1H), 4.72 (m, 1H), 4.41 (t, J=8.5 Hz, 1H), 4.27 (dd, J=2.4, 8.9 Hz, 1H), 3.07 (dd, J=3.1, 13.6 Hz, 1H), 3.00 (dd, J=7.5, 13.6 Hz, 1H), 1.80 (m, 1H), 1.55–1.20 (m, 4H), 0.87 and 0.84 (two overlapping triplets, J=7.6 Hz, 6H); $^{13}$C NMR (DMSO-d$^6$, 100 MHz): δ170.58, 153.48, 136.00, 130.13, 129.26, 127.65, 67.38, 62.74, 55.55, 42.35, 36.86, 22.74, 21.58, 11.54, 11.19; Anal. Calc. for C$_{17}$H$_{22}$N$_4$O$_3$: C, 61.80; H, 6.71. Found: C, 62.53; H, 6.88.

Example 4

2(S)-Azido-3-ethylpentanoic Acid

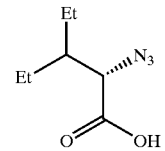

Into a 3 L 3-necked flask equipped with a thermometer, a mechanical stirrer, and a nitrogen inlet tube was placed the product from Example 3 (79 g, 0.239 mol) and THF:H$_2$O (3:1, 1.196 L). The solution was placed under nitrogen, then cooled in an ice/salt bath. After stirring for 50 min, the internal temperature of the reaction mixture was −0.5° C. Lithium hydroxide monohydrate (20.8 g, 0.478 mol) was added at a rate such that the internal temperature of the reaction mixture did not go above 2.5° C. The reaction was monitored by thin layer chromatography. After 1 h, solid sodium bicarbonate (60 g) was added. The reaction mixture was divided into two-0.6 L portions. Each portion was diluted with saturated sodium bicarbonate (80 mL) and water (160 mL), and extracted with ethyl acetate (700 mL). The ethyl acetate layer was washed once more with saturated sodium bicarbonate (160 mL). This ethyl acetate layer contains the chiral auxiliary and was set aside. The combined sodium bicarbonate layers were acidified with 2N hydrochloric acid (600 mL) to pH<2. The acidified aqueous layer was extracted with ethyl acetate (500 mL), then saturated with sodium chloride, and extracted once more with ethyl acetate (500 mL). The combined ethyl acetate layers were dried (Na$_2$SO$_4$), filtered, and concentrated under reduced pressure to give an oil (31.7 g, 77%): Opt. Rot. [α]$_D^{25}$=−82.5° (1% solution, DMSO); $^1$H NMR (DMSO-d$^6$, 500 MHz): δ13.12 (broad s, 1H), 4.26 (d, J=4.3 Hz, 1H), 1.67 (m, 1H), 1.45–1.15 (m, 4H), 0.88 (t, J=7.5 Hz, 3H), 0.83 (t, J=7.5 Hz, 3H); MS(−ESI): [M−H]$^-$, 170 (85%).

Example 5

2(S)-Amino-3-ethylpentanoic Acid

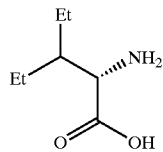

A mixture of the product from Example 4 (31.7 g, 0.185 mol), 10% palladium on carbon (7.9 g), glacial acetic acid (370 mL), and water (926 mL) was placed under an atmosphere of hydrogen (40 psi) and shaken on a Parr hydrogenator. After 20 h, the reaction mixture was filtered through a pad of Celite (½"), which was rinsed well with water (200 mL). The filtrate was concentrated under reduced pressure in a bath heated to 70° C. to produce a white solid. The solid was triturated with ethyl acetate (500 mL), filtered, and washed once more with ethyl acetate (500 mL), and then air dried. This gave the title compound as a white solid (21.2 g, 79%): Opt. Rot. $[\alpha]_D^{25}$=+12.01° (1% solution, $H_2O$); $^1H$ NMR ($D_2O$, 500 MHz): δ4.65 (s, 3H), 3.69 (d, J=3.4 Hz, 1H), 1.69 (m, 1H), 1.44 (m, 1H), 1.03–1.10 (m, 3H), 0.83 and 0.81 (two overlapping triplets, J=7.5 Hz, 6H); MS(−ESI): [M−H]⁻, 144 (100%); Anal. Calc. for $C_7H_{15}NO_2$: C, 57.90; H, 10.41; N, 9.65. Found: C, 57.75; H, 10.89; N, 9.40. Chiral HPLC (Symmetry C18 column, eluant: solvent A=50 mM triethylamine pH adjusted to 3.0 with phosphoric acid, solvent B=AcCN, gradient 80% A/20%B to 50% A/50%B over 20 min, flow rate 1.0 mL/min, detection at 340 nm, S isomer has a retention time of 12.26 min and R isomer has a retention time of 15.46 min) of the amino acid derivatized by Marfey's reagent (N-α-(2,4-dinitro-5-fluorophenyl)-L-alaninamide) gave an enantiomeric ratio of 99.5:0.5 (2S:2R).

Example 6

2(S)-Amino-3-ethylpentanol

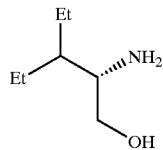

Into a 3 L 3-necked flask equipped with a nitrogen inlet tube, a mechanical stirrer, and an addition funnel with a stopper was placed lithium borohydride (145 mL of a 2 M solution in THF, 0.29 mol). The solution was placed under nitrogen and cooled to 0° C. Chlorotrimethylsilane (73.8 mL, 0.58 mol) was added dropwise over a period of 30 min. The ice bath was removed and the resulting slurry was stirred at room temperature for 30 min. The reaction mixture was cooled to 0° C. and the product from Example 5 (21.1 g, 0.145 mol) was added in portions as a solid over a period of 15 min. The reaction mixture was allowed to warm slowly to room temperature as the ice bath melted. After 3 days at room temperature, the reaction mixture was cooled to 0° C., and methanol (217 mL) was carefully added over a period of 80 min. The solution was stirred at room temperature for an additional 40 min, then concentrated under reduced pressure in a water bath at 60° C. The resulting slurry was made basic with 20% sodium hydroxide (37.5 mL). Water (37.5 mL) was added, and the entire aqueous layer was extracted with methylene chloride (300 mL), and dried ($Na_2SO_4$). Concentration under reduced pressure gave the title compound as an oil (17.3 g, 91%), which was used immediately or stored in the freezer overnight: Opt. Rot. $[\alpha]_D^{25}$=−3.7° (1% solution, DMSO); $^1H$ NMR (DMSO-d⁶, 500 MHz): δ4.38 (broad s, 1H), 3.35 (dd overlapping with a broad s at δ3.32, J=4.5, 10.3 Hz, 3H), 3.14 (dd, J=7.9, 10.2 Hz, 1H), 2.63 (m, 1H), 1.45–1.05 (m, 5H), 0.82 and 0.81(two overlapping triplets, J=7.4 Hz, 6H); MS(+ESI): [M+H]⁺, 132 (60%).

Example 7

5-Chloro-N-[(1S)-2-ethyl-1-(hydroxymethyl)butyl]-2-thiophenesulfonamide

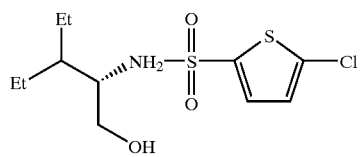

A mixture of 2(S)-amino-3-ethylpentanol (34.1 g, 0.26 mol) and methylene chloride (700 mL) was placed under Argon, and cooled to 0° C. Triethylamine (36.2 mL, 0.26 mol) was added, followed by the dropwise addition of 5-chlorothiophene-2-sulfonyl chloride (56.4 g, 0.26 mol) in methylene chloride (400 mL). The reaction mixture was allowed to warm slowly to room temperature as the ice bath melted. After 3 days at room temperature, the reaction mixture was divided into two-0.6 L portions. Each portion was diluted with ethyl acetate (1 L), and washed three times with saturated potassium phosphate monobasic (200 mL), once with brine (200 mL), and dried ($Na_2SO_4$). Concentration under reduced pressure gave a white solid (74.5 g, 92%). The product (87.98 g) from several runs were combined and recrystallized from hot heptane:ethyl acetate (4:1, 775 mL) to give the title compound as crystals (74.9 g, 85%): mp 115–117.6° C.; Opt. Rot. $[\alpha]_D^{25}$=+10.81° (1% solution, MeOH); $^1H$ NMR (DMSO-d⁶, 500 MHz): δ7.71 (d, J=8.1 Hz, 1H), 7.44 (d, J=4.1 Hz, 1H), 7.22 (d, J=4.1 Hz, 1H), 4.56 (t, J=5.2 Hz, OH), 3.31–3.15 (m, 3H), 1.40–1.15 (m, 4H), 1.07 (m, 1H), 0.79 and 0.76 (two overlapping triplets, J=7.3 Hz, 6H); $^{13}C$ NMR (DMSO-d⁶, 100 MHz): δ141.75, 133.73, 130.95, 127.60, 60.41, 56.89, 41.57, 21.31, 20.80, 11.79, 11.51; MS(−ESI): [M−H]⁻, 1 chlorine isotope pattern, 310 (100%), 312 (30%); Anal. Calc. for $C_{11}H_{18}ClNO_3S_2$: C, 42.37; H, 5.82; N, 4.49. Found: C, 42.34; H, 5.65; N, 4.43. Chiral HPLC (Chiralpak AD, 25×0.46 cm, eluant 8:2 hexane/isopropanol containing 0.1% TFA, flow rate 0.5 mL/min, UV detection at 254 nm, retention times for the S and R isomers are 10.95 min and 11.95 min, respectively) revealed an S/R ratio of 100.0:0.0.

The following compounds were prepared according to the instant invention:

| Ex # | Name |
| --- | --- |
| 1 | 3-ethylpentanoic acid |
| 2 | (3-(2S),4S)-3-(3-ethyl-1-oxopentyl)-4-(phenylmethyl)-2-oxazolidinone |

-continued

| Ex # | Name |
|---|---|
| 3 | (3-(2S),4S)-3-(2-azido-3-ethyl-1-oxopentyl)-4-(phenylmethyl)-2-oxazolidinone |
| 4 | 2(S)-azido-3-ethylpentanoic acid |
| 5 | 2(S)-amino-3-ethylpentanoic acid |
| 6 | 2(S)-amino-3-ethylpentanol |
| 7 | 5-chloro-N-[(1S)-2-ethyl-1-(hydroxymethyl)butyl]-2-thiophenesulfonamide |

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A process for preparing chirally pure S-enantiomers of α-amino acids comprising the steps of:
   a) preparing an organometallic reagent from an alkyl halide of the formula $(R)_2CH(CH_2)_nCH_2X$;
   wherein X is Cl, Br or I and n is 0 to about 10;
   b) adding said organometallic reagent to carbon dioxide to afford a carboxylic acid;
   c) activating said carboxylic acid with an acid halide, phosphorus trichloride, acid anhydride, or thionyl chloride in the presence of a tertiary amine base;
   d) reacting the product of step c) with an alkali metal salt of S-4-benzyl-2-oxazolidinone;
   e) treating the product of step d) with a strong non-nucleophilic base to form an enolate anion;
   f) trapping said enolate anion with 2,4,6-triisopropylbenzenesulfonyl azide to afford an oxazolidinone azide;
   g) hydrolyzing said oxazolidinone azide with an aqueous base to afford an α-azido acid;
   h) reducing said α-azido acid to an α-amino acid; and
   i) recrystallizing said α-amino acid to form said chirally pure α-amino acid.

2. The process according to claim 1, wherein R is ethyl.
3. The process according to claim 1, wherein step b) is accomplished using said acid halide.
4. The process according to claim 3, wherein said acid halide is pivaloyl chloride.
5. The process according to claim 1, wherein said organometallic compound is a Grignard reagent.
6. The process according to claim 1, where said carboxylic acid is of the formula:

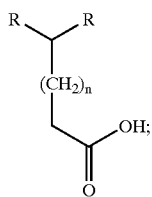

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

7. The process according to claim 1, wherein said carboxylic acid is 3-ethylpentanoic acid.
8. The process according to claim 1, wherein said tertiary amine base is triethylamine.
9. The process according to claim 1, wherein the product of step d) is the following compound:

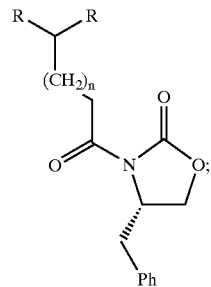

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

10. The process according to claim 1, wherein said product of step d) is (3-(2S), 4S)-3-(3-ethyl-1-oxopentyl)-4-(phenylmethyl)-2-oxazolidinone.
11. The process according to claim 1, wherein said strong non-nucleophilic base is selected from the group consisting of sodium hydride, potassium hydride, lithium diisopropylamide and potassium hexamethyldisilazide.
12. The process according to claim 11, wherein said strong non-nucleophilic base is potassium hexamethyldisilazide.
13. The process according to claim 1, wherein said oxazolidinone azide is of the formula:

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

14. The process according to claim 1, wherein said oxazolidinone azide is (3-(2S), 4S)-3-(2-azido-3-ethyl-1-oxopentyl)-4-(phenylmethyl)-2-oxazolidinone.
15. The process according to claim 1, wherein said aqueous base is selected from the group consisting of lithium hydroxide, potassium hydroxide, and sodium hydroxide.

16. The process according to claim 1, wherein said reducing step h) is accomplished using catalytic reduction with hydrogen gas in the presence of 10% palladium on carbon catalyst.

17. The process according to claim 1, wherein said reducing step h) is accomplished using catalytic hydrogenation, diborane, catecholborane, lithium borohydride/TMSCl, lithium aluminum hydride, DiBAL-H, Red-Al, or alane.

18. The process according to claim 1, where said α-azido acid is of the formula:

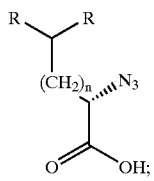

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

19. The process according to claim 1, wherein said α-azido acid is 2(S)-azido-3-ethylpentanoic acid.

20. The process according to claim 1, wherein said α-amino acid is of the formula:

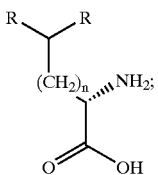

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

21. The process according to claim 1, wherein said α-amino acid is 2(S)-amino-3-ethylpentanoic acid.

22. A process for preparing chirally pure S enantiomers of β-amino alcohols, comprising the steps of:
   a) preparing an organometallic reagent from a halide of the formula $(R)_2CH(CH_2)_nCH_2X$;
   wherein X is Cl, Br or I and n is 0 to about 10;
   b) adding said organometallic reagent to carbon dioxide to afford a carboxylic acid;
   c) activating said carboxylic acid with an acid halide, phosphorus trichloride, acid anhydride, or thionyl chloride in the presence of a tertiary amine base;
   d) reacting the product of step c) with an alkali metal salt of S-4-benzyl-2-oxazolidinone;
   e) treating the product of step d) with a strong non-nucleophilic base to form an enolate anion;
   f) trapping said enolate anion with 2,4,6-triisopropylbenzenesulfonyl azide to afford the oxazolidinone azide;
   g) hydrolyzing said oxazolidinone azide with an aqueous base to afford an α-azido acid;
   h) reducing said α-azido acid to an α-amino acid;
   i) reducing said α-amino acid to an β-amino alcohol; and
   j) recrystallizing said β-amino alcohol to form said chirally pure β-amino alcohol.

23. The process according to claim 22, wherein said β-amino alcohol is of the formula:

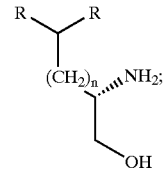

R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

24. The process according to claim 22, wherein said β-amino alcohol is 2(S)-amino-3-ethylpentanol.

25. The process according to claim 22, wherein R is ethyl.

26. The process according to claim 22, wherein step b) is accomplished using said acid halide.

27. The process according to claim 26, wherein said acid halide is pivaloyl chloride.

28. The process according to claim 22, wherein said organometallic compound is a Grignard reagent.

29. The process according to claim 22, where said carboxylic acid is of the formula:

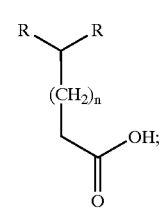

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

30. The process according to claim 22, wherein said carboxylic acid is 3-ethylpentanoic acid.

31. The process according to claim 22, wherein said tertiary amine base is triethylamine.

32. The process according to claim 22, wherein the product of step d) is the following compound:

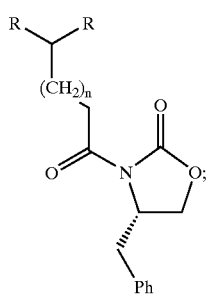

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

33. The process according to claim 22, wherein said product of step d) is (3-(2S), 4 S)-3-(3-ethyl-1-oxopentyl)-4-(phenylmethyl)-2-oxazolidinone.

34. The process according to claim 22, wherein said strong non-nucleophilic base is selected from the group consisting of sodium hydride, potassium hydride, lithium diisopropylamide and potassium hexamethyldisilazide.

35. The process according to claim 34, wherein said strong non-nucleophilic base is potassium hexamethyldisilazide.

36. The process according to claim 22, wherein said oxazolidinone azide is of the formula:

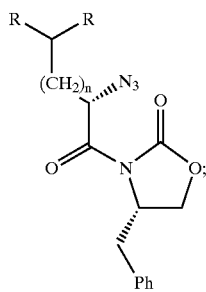

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

37. The process according to claim 22, wherein said oxazolidinone azide is (3-(2S), 4S)-3-(2-azido-3-ethyl-1-oxopentyl)-4-(phenylmethyl)-2-oxazolidinone.

38. The process according to claim 22, wherein said aqueous base is selected from the group consisting of lithium hydroxide, potassium hydroxide, and sodium hydroxide.

39. The process according to claim 22, wherein said reducing step h) is accomplished using catalytic reduction with hydrogen gas in the presence of 10% palladium on carbon catalyst.

40. The process according to claim 22, wherein said reducing step h) is accomplished using catalytic hydrogenation, diborane, catecholborane, lithium borohydride/TMSCl, lithium aluminum hydride, DiBAL-H, Red-Al, or alane.

41. The process according to claim 22, where said α-azido acid is of the formula:

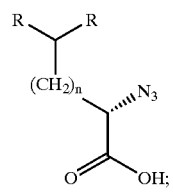

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

42. The process according to claim 22, wherein said α-azido acid is 2(S)-azido-3-ethylpentanoic acid.

43. The process according to claim 22, wherein said α-amino acid is of the formula:

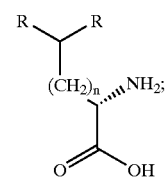

wherein R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

44. The process according to claim 22, wherein said α-amino acid is 2(S)-amino-3-ethylpentanoic acid.

45. A process for preparing chirally pure S enantiomers of N-sulfonyl β-amino alcohols of the general formula:

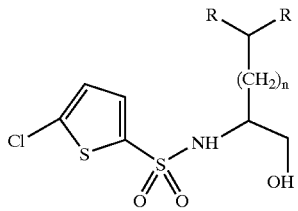

wherein:
R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, CH₂cycloalkyl, CH₂-3-indole, CH(loweralkyl)-2-furan, CH(loweralkyl)-4-methoxyphenyl, CH(loweralkyl)phenyl, and CH(OH)-4-SCH₃-phenyl;

wherein said process comprises the steps of:

a) reducing an α-amino acid to an β-amino alcohol of the formula:

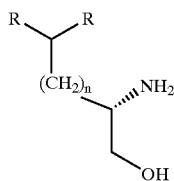

b) sulfonylating said β-amino alcohol with 5-chloro-thiophene-2-sulfonyl halide; and
c) recrystallizing the product of step b) to afford said chirally pure N-sulfonyl β-amino alcohols.

46. The process according to claim 45, wherein said chirally pure N-sulfonyl β-amino alcohol is 5-chloro-N-[(1S)-2-ethyl-1-(hydroxymethyl)butyl]-2-thiophenesulfonamide.

47. A process for preparing chirally pure S enantiomers of N-sulfonyl β-amino alcohols of the general formula:

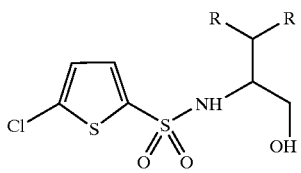

wherein:

R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, CH₂cycloalkyl, CH₂-3-indole, CH(loweralkyl)-2-furan, CH(loweralkyl)-4-methoxyphenyl, CH(loweralkyl)phenyl, and CH(OH)-4-SCH₃-phenyl;

wherein said process comprises the steps of:

a) preparing a Grignard reagent from a halide of the formula (R)₂CHCH₂X;
wherein X is Cl, Br or I;
b) adding said Grignard reagent to carbon dioxide to afford a carboxylic acid of the formula:

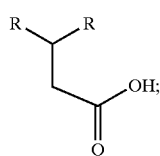

c) activating said carboxylic acid with an acid chloride in the presence of a tertiary amine base;
d) reacting the product of step c) with a lithium salt of S-4-benzyl-2-oxazolidinone to afford the following compound:

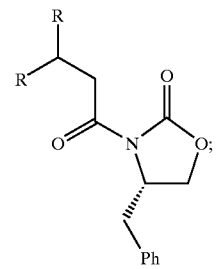

e) treating the product of step d) with potassium hexamethyldisilazide to form an enolate anion;
f) trapping said enolate anion with 2,4,6-triisopropylbenzenesulfonyl azide to afford the oxazolidinone azide of the formula:

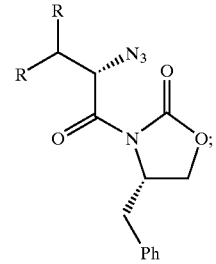

g) hydrolyzing said oxazolidinone azide with an aqueous base selected from the group consisting of lithium hydroxide, potassium hydroxide, and sodium hydroxide to afford an α-azido acid of the formula:

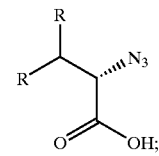

h) reducing said α-azido acid using hydrogen gas in the presence of 10% palladium on carbon catalyst to an α-amino acid of the formula:

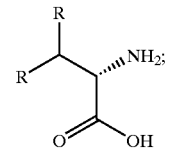

i) reducing said α-amino acid using catalytic hydrogenation, diborane, catecholborane, lithium borohydride/TMSCl, lithium aluminum hydride, DiBAL-H, Red-Al, or alane to an β-amino alcohol of the formula:

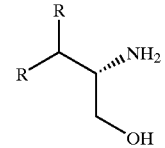

j)سsulfonylating said β-amino alcohol with 5-chloro-thiophene-2-sulfonyl chloride; and
k) recrystallizing the product of step j) to afford said chirally pure N-sulfonyl β-amino alcohols.

* * * * *